United States Patent
Gerhardt (10) Patent No.: US 9,429,548 B2
(45) Date of Patent: Aug. 30, 2016

(54) FLOW SENSORS AND FLOW SENSING METHODS WITH EXTENDED LINEAR RANGE

(75) Inventor: Geoff C. Gerhardt, Milbury, MA (US)

(73) Assignee: Waters Technologies Corporation, Milford, MA (US)

( * ) Notice: Subject to any disclaimer, the term of this patent is extended or adjusted under 35 U.S.C. 154(b) by 1092 days.

(21) Appl. No.: 13/516,684

(22) PCT Filed: Dec. 16, 2010

(86) PCT No.: PCT/US2010/060736
§ 371 (c)(1),
(2), (4) Date: Sep. 27, 2012

(87) PCT Pub. No.: WO2011/075571
PCT Pub. Date: Jun. 23, 2011

(65) Prior Publication Data
US 2013/0013225 A1 Jan. 10, 2013

Related U.S. Application Data

(60) Provisional application No. 61/288,044, filed on Dec. 18, 2009, provisional application No. 61/287,949, filed on Dec. 18, 2009, provisional application No. 61/288,024, filed on Dec. 18, 2009.

(51) Int. Cl.
*G01F 1/00* (2006.01)
*G01F 1/699* (2006.01)
(Continued)

(52) U.S. Cl.
CPC ............. *G01N 30/32* (2013.01); *G01F 1/6845* (2013.01); *G01F 1/00* (2013.01); *G01N 11/00* (2013.01); *G01N 2030/324* (2013.01)

(58) Field of Classification Search
CPC ............. G01N 2030/324; G01F 1/845; G01F 1/8436
USPC .......................................................... 702/45
See application file for complete search history.

(56) References Cited

U.S. PATENT DOCUMENTS 5,515,295 A * 5/1996 Wang .............................. 702/45
6,450,024 B1 * 9/2002 McCulloch et al. ........ 73/204.25
(Continued)

FOREIGN PATENT DOCUMENTS

| WO | 2008080106 A1 | 7/2008 |
| WO | 2011075568 A1 | 6/2011 |
| WO | 2011075570 A1 | 6/2011 |

OTHER PUBLICATIONS

International Preliminary Report on Patentability for PCT/US2010/060729 (WO 2011/075568), issued on Jun. 19, 2012 (7 pages).
(Continued)

*Primary Examiner* — Mischita Henson
*Assistant Examiner* — Christine Liao
(74) *Attorney, Agent, or Firm* — Locke Lord LLP; Brian S. Matross; Nicholas J. DiCeglie, Jr.

(57) ABSTRACT

One aspect of the invention provides a flow sensing apparatus including: a fluid channel that allows a fluid to flow in a first direction; a first temperature sensor arranged at a first position along the fluid channel; a second temperature sensor arranged at a second position along the fluid channel and separated from the first sensor by a predetermined distance along the fluid channel; a heating element arranged between the first and second thermoelectric sensors, the heating element being substantially equally spaced from the first and second thermoelectric sensors; a heating element temperature sensor for sensing a temperature of the heating element; and a control device configured to maintain the heating element at a substantially uniform temperature.

16 Claims, 7 Drawing Sheets

(51) Int. Cl.
*G01N 30/32* (2006.01)
*G01F 1/684* (2006.01)
*G01N 11/00* (2006.01)

(56) References Cited

U.S. PATENT DOCUMENTS

| | | | |
|---|---|---|---|
| 2002/0121137 A1* | 9/2002 | Fujiwara et al. | 73/204.26 |
| 2004/0145049 A1 | 7/2004 | McKinnell et al. | |
| 2004/0163957 A1 | 8/2004 | Neyer et al. | |
| 2005/0109698 A1 | 5/2005 | Gerhardt et al. | |
| 2005/0160833 A1 | 7/2005 | Gerhardt et al. | |
| 2007/0034838 A1 | 2/2007 | Imaoka et al. | |
| 2007/0265689 A1 | 11/2007 | Frey et al. | |
| 2008/0121576 A1 | 5/2008 | Gerhardt et al. | |
| 2008/0145853 A1 | 6/2008 | Wu et al. | |
| 2008/0245136 A1 | 10/2008 | Gerhardt et al. | |
| 2008/0289411 A1* | 11/2008 | Schrag et al. | 73/204.11 |
| 2009/0205409 A1 | 8/2009 | Ciavarini et al. | |
| 2010/0089118 A1* | 4/2010 | Mayer et al. | 73/1.16 |
| 2011/0137580 A1* | 6/2011 | Bartels et al. | 702/47 |

OTHER PUBLICATIONS

International Preliminary Report on Patentability for PCT/US2010/060734 (WO 2011/075570), issued on Jun. 19, 2012 (7 pages).
International Preliminary Report on Patentability for PCT/US2010/060736 (WO 2011/075571), issued on Jun. 19, 2012 (7 pages).
Form PCT/ISA/210, WO, Mar. 2, 2011, International Search Report for PCT/US2010/060736.
Form PCT/ISA/237, WO, Mar. 2, 2011, Written Opinion for PCT/US2010/060736.
Form PCT/ISA/210, WO, Mar. 2, 2011, International Search Report for PCT/US2010/060729.
Form PCT/ISA/210, WO, Feb. 16, 2011, International Search Report for PCT/US2010/060734.

\* cited by examiner

FLOW SENSORS AND FLOW SENSING METHODS WITH EXTENDED LINEAR RANGE

RELATED APPLICATIONS

This application is the U.S. national phase, pursuant to 35 U.S.C. §371, of PCT international application Ser. No. PCT/US2010/060736, filed Dec. 16, 2010, designating the United States and published in English on Jun. 23, 2011 as publication WO 2011/075571 A1, which claims priority to U.S. provisional patent application Ser. Nos. 61/287,949, filed Dec. 18, 2009; 61/288,024, filed Dec. 18, 2009; and 61/288,044, filed Dec. 18, 2009. The entire disclosures of the aforementioned patent applications are incorporated herein by this reference.

BACKGROUND OF THE INVENTION

All flow sensors that employ the differential thermal anemometry technique suffer from a limited linear range.

Figure 1:
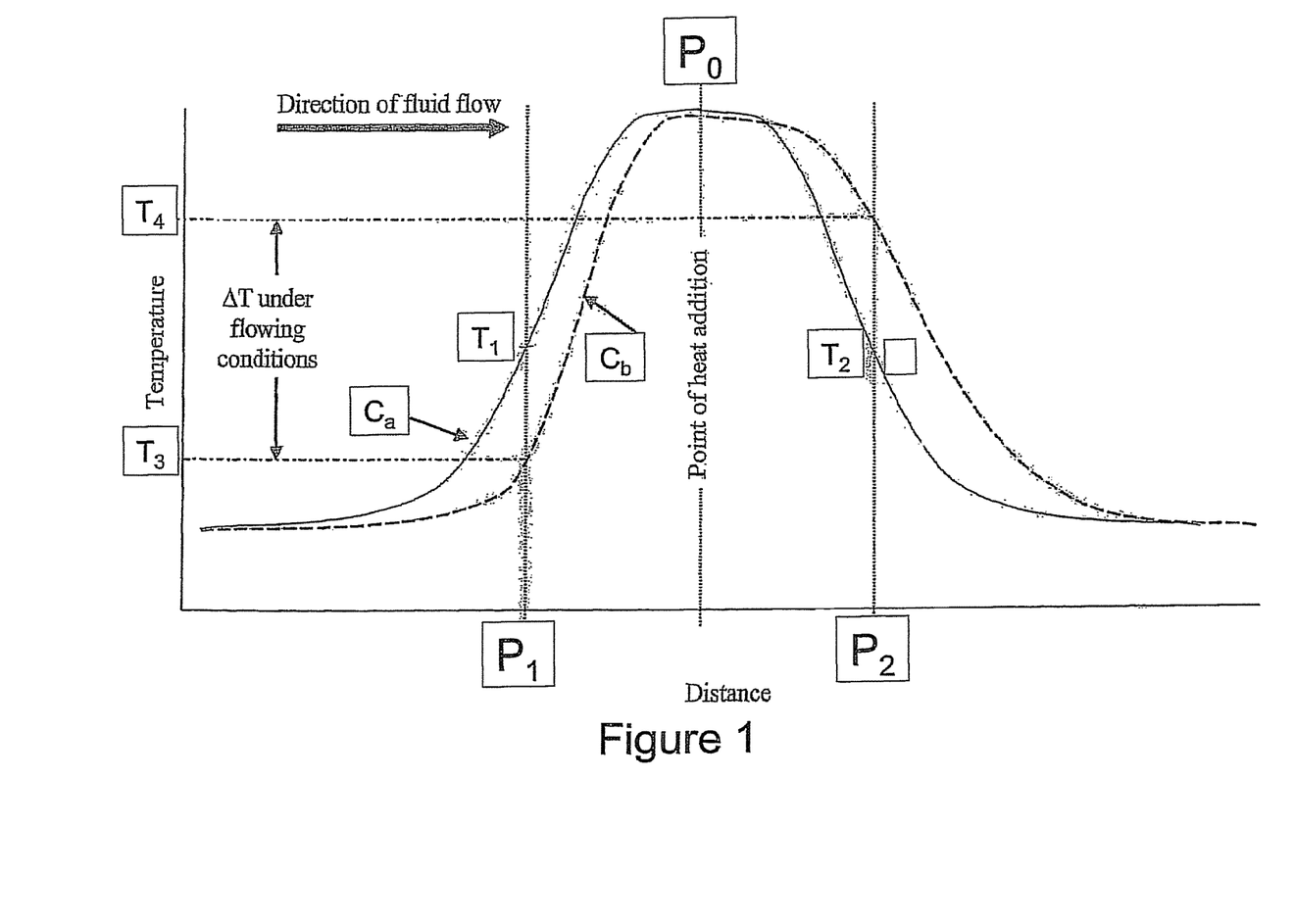
FIG. 1 is a conceptual view of the thermal flow sensing measurements.

Typically, these are thermal flow sensors that operate as shown in FIG. 1. A discrete thermal plug introduced into a liquid filled tube/channel will disperse in both the upstream and downstream directions due to thermal conduction or diffusion, respectively. In the case where a discrete section of the fluid in the tube/channel is continuously heated, a temperature profile similar to $C_a$ in FIG. 1 will develop (i.e., a zero flow condition). The shape of this temperature profile will depend upon the amount of heat added to the fluid and the upstream and downstream temperatures of the liquid. Assuming identical upstream and downstream fluid temperatures, under this zero-flow condition, liquid temperatures measured at $P_1$ and $P_2$ will be equal as thermal diffusion will be equal in both directions. If the liquid in the tube/channel is permitted to flow, the fluid temperatures at $P_1$ and $P_2$ will now also depend upon the rate of liquid flux and the resulting heat convection. As liquid begins to flow past the heated zone, a temperature profile similar to $C_B$ in FIG. 1 will develop since, in addition to the symmetrical diffusion of the heat, asymmetrical convection of the heated fluid will occur in the direction of the fluid flow. Therefore, under flowing conditions, fluid temperatures measured at $P_1$ and $P_2$ will be different. Temperature measurements made at $P_1$ and $P_2$ can be sampled, subtracted and amplified electronically in situ to allow a high degree of common-mode noise rejection which will allow discrimination of extremely small upstream and downstream temperature differences.

Although the differential temperature is proportional to flow at low flow rates, at elevated flow rates, this relationship becomes nonlinear. At low flow rates, the temperature of the heater is essentially constant as the convection of heat carried away from the heater due to the flowing liquid is relatively small. A thermal flow sensor operated in this low flow range has essentially a linear response of upstream/downstream $\Delta T$ with flow. At higher flow rates, this convective heat removal from the heater becomes non-trivial. If constant power is applied to the heater, its temperature will decrease. As the temperature of the heater decreases, the upstream/downstream temperatures will necessarily converge and the $\Delta T$ response to flow rate changes will decrease. At extremely high flow rates, this convection will become so large that an increase in flow rate will actually cause a decrease in $\Delta T$.

It is this phenomenon that limits the effective range of any sensor design based on thermal anemometry. It is not uncommon for flow sensors to be used outside their linear range by using a polynomial function to linearize the raw sensor response. While this is effective, it requires processing of the analog signal and can only extend the flow sensor range to the point where the $\Delta T$ response to flow is still measurable and positive. Also, while a flow sensor can be designed appropriately to handle large fluid flows without decreasing the heater temperature, this typically requires a more massive heater with larger surface area to be used. Such a heater would make the sensor unsuitable for measuring low fluid flow rates as its response to flow changes would be very slow.

Accordingly, there is a need for devices and methods that extend the linear range of flow sensing apparatus for both low and high flow applications.

SUMMARY OF THE INVENTION

One aspect of the invention provides a method for determining a flow rate through a flow sensor including a conduit, a first temperature sensor positioned along the conduit, a second temperature sensor positioned along the conduit, a heating element positioned substantially equidistant between the first temperature sensor and the second temperature sensor along the conduit, and a heating element temperature sensor. The method includes: actuating the heating element; receiving temperature information from the first temperature sensor and the second temperature sensor at a zero flow rate; flowing a first known flow rate through the flow sensor to calculate a flow scalar value; flowing a second known flow rate through the flow sensor, the second known flow rate exceeding a maximum linear range flow rate of the flow sensor; receiving temperature information from the first temperature sensor, the second temperature sensor, and the heating element temperature sensor; computing a heating element compensation factor based the temperature information received from the first temperature sensor, the second temperature sensor, and the heating element temperature sensor; flowing a fluid sample through the flow sensor; and calculating a flow rate based on a difference in temperatures between the first temperature sensor and the second temperature sensor, temperature information from the heating element temperature sensor, the flow scalar value, and the heating element compensation factor, thereby determining a flow rate through the flow sensor.

This aspect of the invention can have a variety of embodiments. The method can further include the steps of: calculating a difference $\Delta T_0$ between the second temperature sensor and the first temperature sensor at a zero flow state; and receiving a temperature $H_0$ of the heating element at the zero flow state from the heating element temperature sensor.

The method can further include the step of: calculating a difference $\Delta T$ between the second temperature sensor and the first temperature sensor while the flow sensor is exposed to the first known flow rate. The first known flow rate can be substantially equal to a maximum linear range flow rate of the fluid sensor.

The flow scalar value can be calculated by dividing the known flow rate by the difference between $\Delta T$ and $\Delta T_0$.

The method can further include the step of: receiving a temperature H of the heating element from the heating element temperature sensor while the flow sensor is exposed to the second known flow rate. The heating element compensation factor can be defined by the expression $(1+\alpha(H_0-H))$, wherein $\alpha$ is a constant according to an expression $$\alpha = \frac{\frac{F}{\Delta T - \Delta T_0} - 1}{H_0 - H},$$

and wherein F is the second known flow rate. The second known flow rate F can be about three times the maximum linear range flow rate of the fluid sensor.

The flow rate can be defined by $(\Delta T - \Delta T_0)(1 + \alpha(H_0 - H))$ times the flow scalar value.

Another aspect of the invention provides a flow sensing apparatus including: a fluid channel that allows a fluid to flow in a first direction; a first temperature sensor arranged at a first position along the fluid channel; a second temperature sensor arranged at a second position along the fluid channel and separated from the first sensor by a predetermined distance along the fluid channel; a heating element arranged between the first and second temperature sensors, the heating element being substantially equally spaced from the first and second temperature sensors; a heating element temperature sensor arranged to measure the temperature of the heating element; and a computing device. The computing device can be configured to: calculate a flow scalar value based on temperature information received from the first temperature sensor and the second temperature while the flow sensor is exposed to a first known flow rate; calculate a heating element compensation factor based the temperature information received from the first temperature sensor, the second temperature sensor, and the heating element temperature sensor while the flow sensor is exposed to a second known flow rate; and calculate a flow rate based on outputs from the first temperature sensor, the second temperature sensor, and the heating element temperature sensor, the flow scalar value, and the heating element compensation factor.

This aspect of the invention can have a variety of embodiments. The computing device can be further configured to: calculate a difference $\Delta T_0$ between the second temperature sensor and the first temperature sensor at a zero flow state; and obtain a temperature $H_0$ of the heating element at the zero flow state from the heating element temperature sensor.

The computing device can be further configured to calculate a difference $\Delta T$ between the second temperature sensor and the first temperature sensor at a non-zero flow state The computing device can be further configured to calculate the flow scalar value by dividing a first known flow rate by the difference between $\Delta T$ and $\Delta T_0$. The first known flow rate can be substantially equal to a maximum linear range flow rate of the fluid sensor.

The computing device can be further configured to obtain a temperature H of the heating element at the non-zero flow state from the heating element temperature sensor. The heating element compensation factor can be defined by the expression $(1 + \alpha(H_0 - H))$, wherein $\alpha$ is a constant according to an expression $$\alpha = \frac{\frac{F}{\Delta T - \Delta T_0} - 1}{H_0 - H},$$

and wherein F is the second known flow rate. The second known flow rate F can be about three times the maximum linear range flow rate of the fluid sensor.

The flow rate can be defined by $(\Delta T - \Delta T_0)(1 + \alpha(H_0 - H))$ times the flow scalar value.

Another aspect of the invention provides a flow sensing apparatus including: a fluid channel that allows a fluid to flow in a first direction; a first temperature sensor arranged at a first position along the fluid channel; a second temperature sensor arranged at a second position along the fluid channel and separated from the first sensor by a predetermined distance along the fluid channel; a heating element arranged between the first and second thermoelectric sensors, the heating element being substantially equally spaced from the first and second thermoelectric sensors; a heating element temperature sensor for sensing a temperature of the heating element; and a control device configured to maintain the heating element at a substantially uniform temperature.

This aspect of the invention can have a variety of embodiments. The control device can be an operational amplifier. The control device can be a proportional-integral-derivative (PID) device.

Another aspect of the invention provides a method for determining a flow rate through a flow sensor including a conduit, a first temperature sensor positioned along the conduit, a second temperature sensor positioned along the conduit, a heating element positioned substantially equidistant between the first temperature sensor and the second temperature sensor along the conduit, and a heating element temperature sensor. The method includes: flowing a fluid sample through the flow sensor; maintaining the heating element at a substantially uniform temperature; receiving temperature information from the first temperature sensor and the second temperature sensor; and calculating a flow rate based on a difference in temperatures between the first temperature sensor and the second temperature sensor, thereby determining a flow rate through the flow sensor.

Another aspect of the invention provides a kit including: (a) a flow sensing apparatus comprising: a fluid channel that allows a fluid to flow in a first direction; a first temperature sensor arranged at a first position along the fluid channel; a second temperature sensor arranged at a second position along the fluid channel and separated from the first sensor by a predetermined distance along the fluid channel; a heating element arranged between the first and second temperature sensors, the heating element being substantially equally spaced from the first and second temperature sensors; a heating element temperature sensor arranged to measure the temperature of the heating element; and a computing device; and (b) instructions for installation and/or use. The computing device can be configured to: calculate a flow scalar value based on temperature information received from the first temperature sensor and the second temperature sensor while the flow sensor is exposed to a first known flow rate; calculate a heating element compensation factor based the temperature information received from the first temperature sensor, the second temperature sensor, and the heating element temperature sensor while the flow sensor is exposed to a second known flow rate; and calculate a flow rate based on outputs from the first temperature sensor, the second temperature sensor, and the heating element temperature sensor, the flow scalar value, and the heating element compensation factor.

Another aspect of the invention provides a High Performance Liquid Chromatography (HPLC) device including a flow sensing apparatus comprising: a fluid channel that allows a fluid to flow in a first direction; a first temperature sensor arranged at a first position along the fluid channel; a second temperature sensor arranged at a second position along the fluid channel and separated from the first sensor by a predetermined distance along the fluid channel; a heating element arranged between the first and second temperature sensors, the heating element being substantially equally spaced from the first and second temperature sensors; a heating element temperature sensor arranged to measure the temperature of the heating element; and a computing device. The computing device can be configured to: calculate a flow scalar value based on temperature information received from the first temperature sensor and the second temperature sensor while the flow sensor is exposed to a first known flow rate; calculate a heating element compensation factor based the temperature information received from the first temperature sensor, the second temperature sensor, and the heating element temperature sensor while the flow sensor is exposed to a second known flow rate; and calculate a flow rate based on outputs from the first temperature sensor, the second temperature sensor, and the heating element temperature sensor, the flow scalar value, and the heating element compensation factor.

Another aspect of the invention provides a kit including: (a) a flow sensing apparatus comprising: a fluid channel that allows a fluid to flow in a first direction; a first temperature sensor arranged at a first position along the fluid channel; a second temperature sensor arranged at a second position along the fluid channel and separated from the first sensor by a predetermined distance along the fluid channel; a heating element arranged between the first and second thermoelectric sensors, the heating element being substantially equally spaced from the first and second thermoelectric sensors; a heating element temperature sensor for sensing a temperature of the heating element; and a control device configured to maintain the heating element at a substantially uniform temperature; and (b) instructions for installation and/or use.

Another aspect of the invention provides a High Performance Liquid Chromatography (HPLC) device including a flow sensing apparatus comprising: a fluid channel that allows a fluid to flow in a first direction; a first temperature sensor arranged at a first position along the fluid channel; a second temperature sensor arranged at a second position along the fluid channel and separated from the first sensor by a predetermined distance along the fluid channel; a heating element arranged between the first and second thermoelectric sensors, the heating element being substantially equally spaced from the first and second thermoelectric sensors; a heating element temperature sensor for sensing a temperature of the heating element; and a control device configured to maintain the heating element at a substantially uniform temperature.

Another aspect of the invention provides a method for determining a flow rate through a flow sensor including a conduit, a first temperature sensor positioned along the conduit, a second temperature sensor positioned along the conduit, a heating element positioned substantially equidistant between the first temperature sensor and the second temperature sensor along the conduit, and a heating element temperature sensor. The method includes: actuating the heating element; receiving temperature information from the first temperature sensor and the second temperature sensor at a zero flow state; calculating a difference $\Delta T_0$ between the second temperature sensor and the first temperature sensor at a zero flow state; receiving a temperature $H_0$ of the heating element at the zero flow state from the heating element temperature sensor; flowing a first known flow rate through the flow sensor to calculate a flow scalar value, the first known flow rate within a maximum linear range flow rate of the flow sensor; calculating a difference $\Delta T$ between the second temperature sensor and the first temperature sensor while the flow sensor is exposed to a first known flow rate; flowing a second known flow rate through the flow sensor, the second known flow rate exceeding a maximum linear range flow rate of the flow sensor; receiving temperature information from the first temperature sensor, the second temperature sensor, and the heating element temperature sensor while the flow sensor is exposed to the second known flow rate; computing a heating element compensation factor based the temperature information received from the first temperature sensor, the second temperature sensor, and the heating element temperature sensor while the flow sensor is exposed to the second known flow rate; flowing a fluid sample through the flow sensor; and calculating a flow rate based on a difference in temperatures between the first temperature sensor and the second temperature sensor, temperature information from the heating element temperature sensor, the flow scalar value, and the heating element compensation factor, thereby determining a flow rate through the flow sensor.

This aspect can have a variety of embodiments. The first known flow rate can be substantially equal to a maximum linear range flow rate of the fluid sensor. The second known flow rate is between about 2.5 and 3.5 times the maximum linear range flow rate of the fluid sensor. The second known flow rate can be three times the maximum linear range flow rate of the fluid sensor.

The heating element compensation factor can be defined by the expression $(1+\alpha(H_0-H))$, wherein $\alpha$ is a constant according to an expression $$\alpha = \frac{\frac{F}{\Delta T - \Delta T_0} - 1}{H_0 - H},$$

and wherein F is the second known flow rate.

The flow rate can be defined by $(\Delta T - \Delta T_0)(1+\alpha(H_0-H))$ times the flow scalar value.

Another aspect of the invention provides a computer program product including computer-usable medium having control logic stored therein for causing a computer to perform a method of determining a flow rate through a flow sensor including a conduit, a first temperature sensor positioned along the conduit, a second temperature sensor positioned along the conduit, a heating element positioned substantially equidistant between the first temperature sensor and the second temperature sensor along the conduit, and a heating element temperature sensor. The control logic includes: first computer readable program code means for causing the computer to actuate the heating element; second computer readable program code means for causing the computer to receive temperature information from the first temperature sensor and the second temperature sensor at a zero flow rate; third computer readable program code means for causing the computer to flow a first known flow rate through the flow sensor to calculate a flow scalar value; fourth computer readable program code means for causing the computer to flow a second known flow rate through the flow sensor, the second known flow rate exceeding a maximum linear range flow rate of the flow sensor; fifth computer readable program code means for causing the computer to receive temperature information from the first temperature sensor, the second temperature sensor, and the heating element temperature sensor; sixth computer readable program code means for causing the computer to compute a heating element compensation factor based the temperature information received from the first temperature sensor, the second temperature sensor, and the heating element temperature sensor; seventh computer readable program code means for causing the computer to flow a fluid sample through the flow sensor; and eighth computer readable program code means for causing the computer to calculate a flow rate based on a difference in temperatures between the first temperature sensor and the second temperature sensor, temperature information from the heating element temperature sensor, the flow scalar value, and the heating element compensation factor.

Another aspect of the invention provides a computer program product including computer-usable medium having control logic stored therein for causing a computer to perform a method of determining a flow rate through a flow sensor including a conduit, a first temperature sensor positioned along the conduit, a second temperature sensor positioned along the conduit, a heating element positioned substantially equidistant between the first temperature sensor and the second temperature sensor along the conduit, and a heating element temperature sensor. The control logic includes: first computer readable program code means for causing the computer to flow a fluid sample through the flow sensor; second computer readable program code means for causing the computer to maintain the heating element at a substantially uniform temperature; third computer readable program code means for causing the computer to receive temperature information from the first temperature sensor and the second temperature sensor; and fourth computer readable program code means for causing the computer to calculate a flow rate based on a difference in temperatures between the first temperature sensor and the second temperature sensor.

Another aspect of the invention provides a computer program product including computer-usable medium having control logic stored therein for causing a computer to perform a method of determining a flow rate through a flow sensor including a conduit, a first temperature sensor positioned along the conduit, a second temperature sensor positioned along the conduit, a heating element positioned substantially equidistant between the first temperature sensor and the second temperature sensor along the conduit, and a heating element temperature sensor. The control logic includes: first computer readable program code means for causing the computer to actuate the heating element; second computer readable program code means for causing the computer to receive temperature information from the first temperature sensor and the second temperature sensor at a zero flow state; third computer readable program code means for causing the computer to calculate a difference $\Delta T_0$ between the second temperature sensor and the first temperature sensor at a zero flow state; fourth computer readable program code means for causing the computer to obtain a temperature $H_0$ of the heating element at the zero flow state from the heating element temperature sensor; fifth computer readable program code means for causing the computer to flow a first known flow rate through the flow sensor to calculate a flow scalar value, the first known flow rate within a maximum linear range flow rate of the flow sensor; sixth computer readable program code means for causing the computer to calculate a difference $\Delta T$ between the second temperature sensor and the first temperature sensor at a non-zero flow state; seventh computer readable program code means for causing the computer to flow a second known flow rate through the flow sensor, the second known flow rate exceeding a maximum linear range flow rate of the flow sensor; eighth computer readable program code means for causing the computer to receive temperature information from the first temperature sensor, the second temperature sensor, and the heating element temperature sensor while the flow sensor is exposed to the second known flow rate; ninth computer readable program code means for causing the computer to compute a heating element compensation factor based the temperature information received from the first temperature sensor, the second temperature sensor, and the heating element temperature sensor while the flow sensor is exposed to the second known flow rate; tenth computer readable program code means for causing the computer to flow a fluid sample through the flow sensor; and eleventh computer readable program code means for causing the computer to calculate a flow rate based on a difference in temperatures between the first temperature sensor and the second temperature sensor, the flow scalar value, and the heating element compensation factor.

BRIEF DESCRIPTION OF THE DRAWINGS

For a fuller understanding of the nature and desired objects of the present invention, reference is made to the following detailed description taken in conjunction with the accompanying drawing figures wherein like reference character denote corresponding parts throughout the several views and wherein.

DETAILED DESCRIPTION OF THE INVENTION

Definitions

The instant invention is more clearly understood with reference to the following definitions:

As used in the specification and claims, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. The term "about" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

A computer-readable medium shall be understood to mean any article of manufacture that contains data that can be read by a computer or a carrier wave signal carrying data that can be read by a computer. Such computer-readable media includes, but is not limited to, magnetic media, such as a floppy disk, a flexible disk, a hard disk, reel-to-reel tape, cartridge tape, cassette tape or cards; optical media such as CD-ROM and writeable compact disc; magneto-optical media in disc, tape or card form; paper media, such as punched cards and paper tape; or on carrier wave signal received through a network, wireless network or modem, including radio-frequency signals and infrared signals.

Unless specifically stated or obvious from context, as used herein, the term "or" is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

Thermal flow sensor according to the subject invention utilizes the thermoelectric effect to convert thermal convection due to a flowing fluid into a voltage response that is proportional to the fluid flow rate.

FIG. 1 depicts fluid temperature measurements along a fluid filled fluid channel as thermal energy is introduced at a fixed location along the fluid channel. When thermal energy is introduced into a liquid filled fluid channel at location $P_0$ along the channel, the thermal energy will disperse along the channel in both the upstream and downstream directions due to thermal conduction and diffusion. In FIG. 1, the vertical axis denotes measured temperature and the horizontal axis denotes distance along the fluid channel. A temperature profile, curve $C_a$ will develop when a discrete section of the fluid in the fluid channel is continuously heated by a heating element while the fluid is resting or under a so-called zero-flow condition. The shape of this temperature profile depends on the amount of heat added to the fluid and the upstream and downstream temperatures of the liquid. Assuming identical upstream and downstream fluid temperatures and a zero-flow condition, liquid temperatures $T_1$ and $T_2$ measured at the first and second sensors that are placed at equal distances upstream and downstream from $P_0$, denoted by $P_1$ and $P_2$, will be equal as thermal conduction and diffusion will be approximately equal.

If liquid in the fluid channel is permitted to flow, the fluid temperatures at the first and second locations $P_1$ and $P_2$ will depend upon the flow rate of liquid and the resulting heat convection. Curve $C_b$ of FIG. 1 depicts a temperature profile as liquid begin to flow past $P_0$, or the heated zone. Note that while Ca is substantially symmetrical about $P_0$, $C_b$ is not symmetrical about $P_0$. This is due to an asymmetric convection of the heated fluid that occurs in the direction of the fluid flow. Therefore, under flowing conditions, fluid temperatures $T_3$ and $T_4$ measured at $P_1$ and P2, respectively, will be different from $T_1$ and $T_2$. A difference of $T_3$ and $T_4$, denoted by $\Delta T$, may be calculated and correlated to the actual flow rate of the fluid that flowed inside the fluid channel.

To perform the above-mentioned temperature measurements, a number of sensing methods and apparatuses can be used. Generally, two temperature sensors are disposed along a fluid channel at equal distances upstream and downstream from the heating element. For example, as shown in FIG. 1, $P_1$ and $P_2$ were chosen to be the inflection points of the temperature profile $C_a$. Measurement at the inflection points can minimize the amount of time required to detect a difference between measured temperatures $T_1$ and $T_3$ or the difference between the temperatures $T_2$ and $T_4$ and thus maximize the upstream/downstream $\Delta T$ response of an amplifier element to flow rate change.

Figure 2:
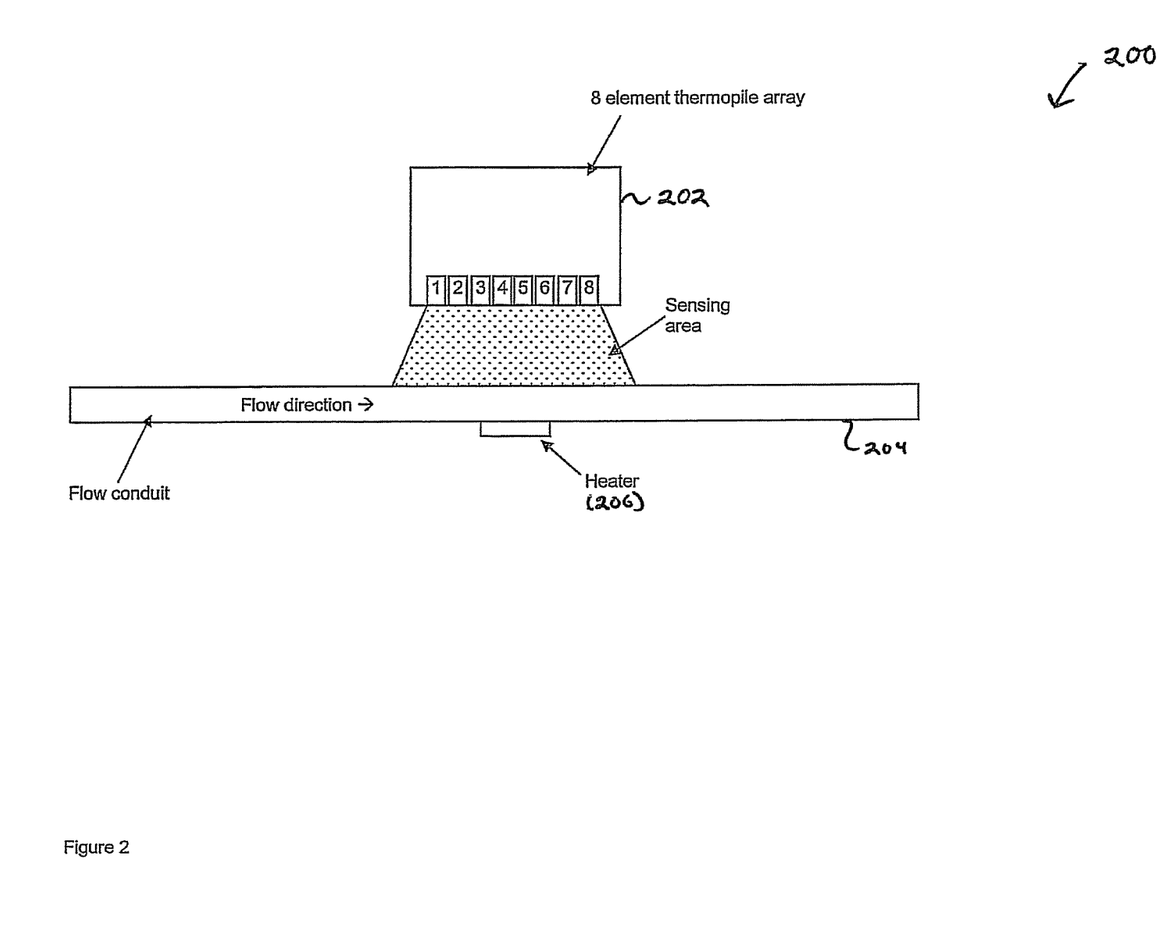
FIG. 2 depicts a flow sensor according to one embodiment of the invention.

Referring now to FIG. 2, in order to better understand the non-linear behavior of thermal-based flow sensors and the effect of convective cooling of the heater, a DEVANTECH™ TPA81 thermopile array 202 was used to thermally image a centrally heated tube 204 under flowing conditions. This multi-element array measures both the up- and downstream temperatures of the tube 204 and the temperature of heater 206.

To measure flow by conventional flow anemometry using non-contact sensor array 202, the upstream flow temperature used was the average of elements 1, 2 and 3 of the sensor array 202, and the downstream temperature was the average of elements 6, 7 and 8. Expressed numerically:

$$\Delta T = \frac{(T_6 + T_7 + T_8) - (T_1 + T_2 + T_3)}{3} \tag{1}$$

$$\text{FlowRate} = (\Delta T - \Delta T_0) \times \text{FlowScalar} \tag{2}$$

The $\Delta T_0$ value is used to balance the flow sensor 200 and adjust for any misalignment of the sensor array 202 and heater 206 such that at zero flow, the difference between upstream and downstream temperatures is zero. The FlowScalar value can be adjusted depending on the material used for the flow tube (e.g., to reflect thermal conductivity) and the fluid flowing through the tube 204.

Figure 3:
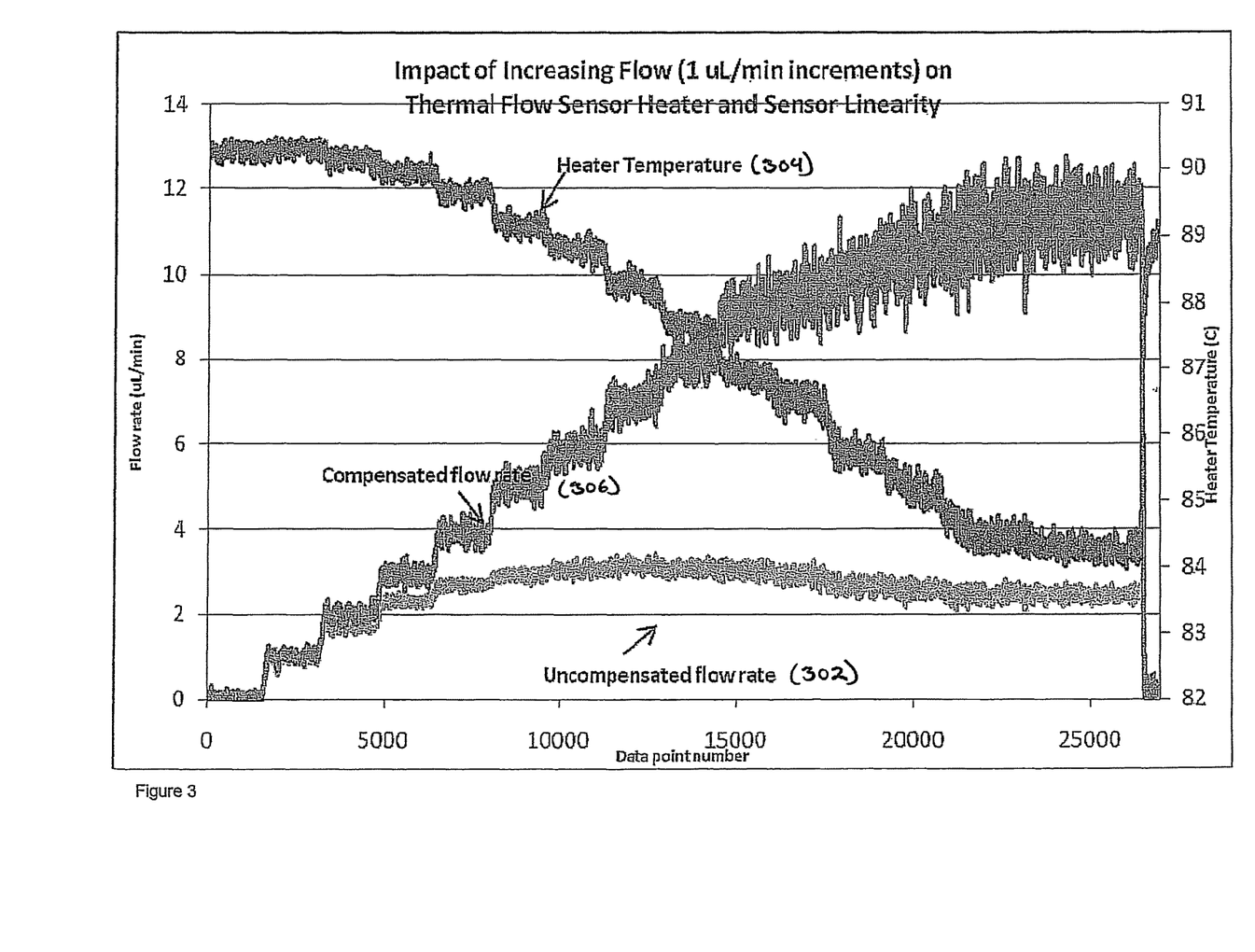
FIG. 3 is a plot of uncompensated flow rate, compensated flow rate, and heater temperature according to one embodiment of the invention.

FIG. 3 depicts processed data collected using system 200 depicted in FIG. 2. The data shown in FIG. 3 was collected when water was flowing through the tube 204. The flow rate was initially 0 µL/min and was then successively increased by 1 µL/min increments. The light grey plot 302 depicts the flow response when according to the formulas provided above. When the flow is under 1-1.5 µL/min, the flow response is linear, but as the flow is increased, the flow response becomes increasingly nonlinear. Because the sensor array 202 is also monitoring the heater temperature, as the flow increases and the heater 206 begins to cool, the flow response departs from linearity. (The "Heater Temperature" plot 304 in FIG. 3 is the average of sensors 4 and 5 of the array 202, which are positioned directly over the heater element 206). This decrease in heater temperature 304 is due to the convection of the fluid over the heater 206. Because the heater temperature 304 is decreasing, the temperature upstream/downstream difference will be reduced, which leads to the flow response nonlinearity. Equation (2) above multiplies the difference between the temperatures upstream and downstream of the heater by a scalar to determine the flow rate. As shown in plot 304 in FIG. 3, this produces a linear response only in the flow region where the heater is not substantially cooled by the fluid flow. While this is effective, the maximum flow that can be measured is where the flow response asymptotes.

Embodiments of the invention measure the heater temperature and compensate the measured temperature difference for any decrease in the heater temperature using a unitless compensation factor:

$$\text{CompensatedFlowRate} = (\Delta T - \Delta T_0)(1 + \alpha(H_0 - H)) \times \text{FlowScalar} \tag{3}$$

In the equation above, a heater compensation factor α is used to adjust the measured ΔT as the temperature of the heater 206 decreases due to convective cooling. Before the flow sensor is used, it is first "zeroed" by measuring both the ΔT and heater temperature H at zero flow. These values are stored as $\Delta T_0$ and $H_0$. As the flow increases and the measured heater temperature H decreases below $H_0$, the heater compensation $(1+\alpha(H_0-H))$ will return a value>1 to scale the ΔT and increase its value to accommodate for the decreasing heater temperature.

Normal flow sensor calibration involves first zeroing the sensor, then flowing a known flow rate through the sensor to establish the FlowScalar value. Embodiments of the invention improve upon prior calibration techniques by introducing a third operation that sets a heater compensation factor α.

After the sensor 200 is zeroed, a known flow is delivered to the flow sensor 200 at the maximum of the linear range of the sensor 200. In the linear range of the sensor 200, the heater temperature H should be equal to $H_0$, so the heater compensation $(1+\alpha(H_0-H))$ equals 1. Using this flow rate in the flow sensor linear range, the FlowScalar can be set according to Equations (4)-(6) below:

$$H_0 - H = 0 \quad (4)$$

$$\therefore \text{FlowRate} = (\Delta T - \Delta T_0)(1) \times \text{FlowScalar} \quad (5)$$

$$\text{FlowScalar} = \frac{\text{FlowRate}}{\Delta T - \Delta T_0} \quad (6)$$

Once FlowScalar is set, heater compensation factor α is set by flowing a flow rate preferably at approximately three times the maximum linear range through the flow sensor 200 to solve Equation (7):

$$\alpha = \frac{\frac{\text{FlowRate}}{\Delta T - \Delta T_0} - 1}{H_0 - H} \quad (7)$$

Once the flow sensor 200 is zeroed, and FlowScalar and heater compensation factor α are set, equation (1) can be used to determine flow rate given the upstream/downstream and heater temperatures. The compensated flow rate plot 306 in FIG. 3 depicts the linearity range extended significantly by using this technique. While there is significant noise in the signal shown in these plots, it should be realized that the TPA81 sensor 200 used for experimentation is not particularly sensitive and was used during the development of this technique to understand the thermal distribution along the flow tube 204. In implementation of the invention, more sensitive temperature sensors can be placed directly on the flow tube 204 and heater 206 to sense the upstream/downstream and heater temperatures.

The technique described above compensates the flow response for the decrease in heater temperature that results from a high-flow operation. Another embodiment of the invention maintains the heater 206 at a constant temperature. Since the primary reason for the non-linear ΔT-flow response is cooling of the central heater 206 at high flow rates, any approach that maintains the heater 206 at a constant temperature in spite of high convective currents improves the linear range of the flow sensor 200.

Figure 4:
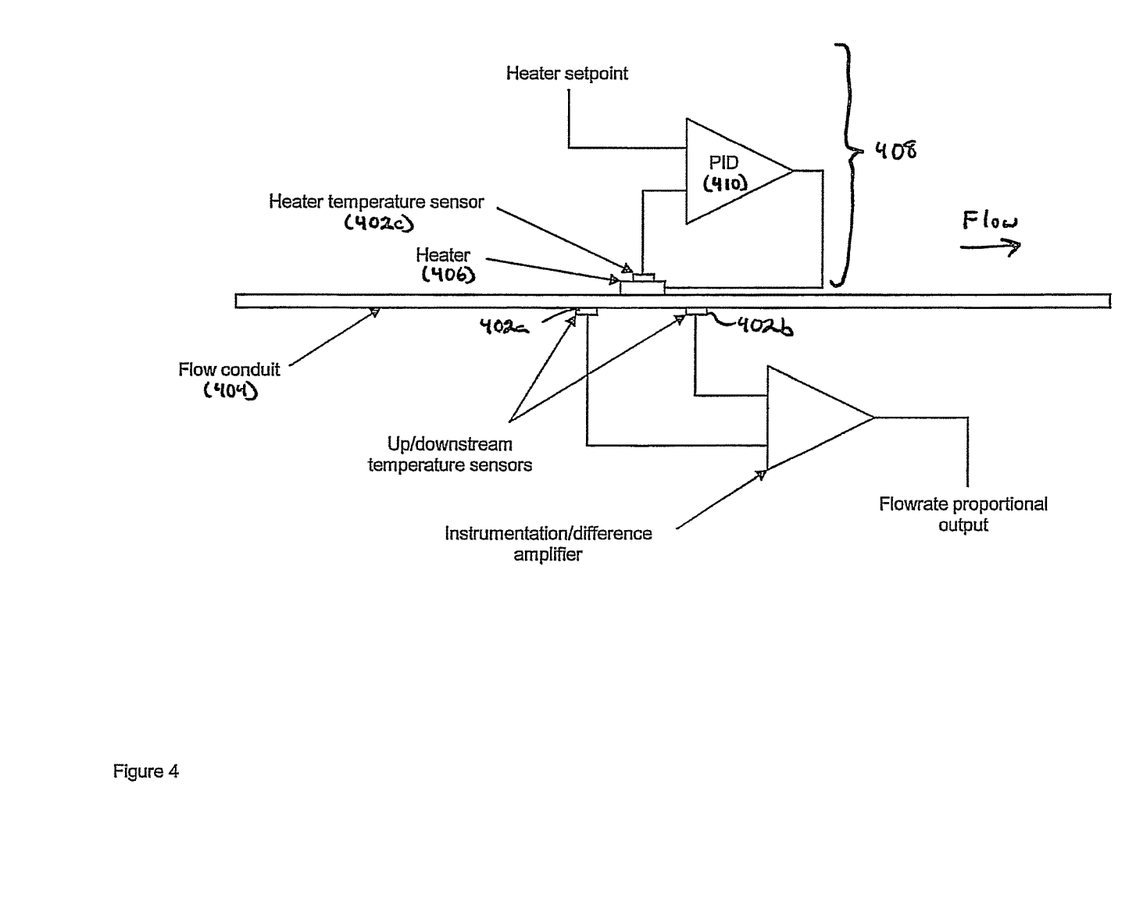
FIG. 4 depicts a flow sensor according to one embodiment of the invention.

The first embodiment of a temperature-stabilized heater flow sensor is shown in FIG. 4. In FIG. 4, a thermal-based flow sensor 400 is shown. In addition to upstream and downstream temperature sensors 402a, 402b, a third temperature sensor 402c is placed on or close to the central heater 406 to monitor the heater temperature. An external closed-loop circuit 408 is used to control the heater temperature to a pre-defined set-point. This control circuit can be implemented by an analog op-amp with feedback or a proportional-integral-derivative (PID) system 410 as depicted in FIG. 4. As the flow rate increases and convection cools the heater 406, the closed-loop circuit 408 supplies more current to the heater 406 to maintain the set-point temperature.

The heater temperature sensor 402c can be placed directly on the back of the heater 406. Alternatively, the heater temperature sensor 402c is placed in direct contact with the fluid in conduit 404 to achieve high fidelity to the actual temperature of the fluid at $P_0$. Such an embodiment may not always be practical. Accordingly, placing the heater feedback temperature sensor 402c on opposite the side of the tube/conduit 404 can, in some embodiments, provide better feedback to correct for convective losses than simply placing it directly on the heater 406.

Figure 5:
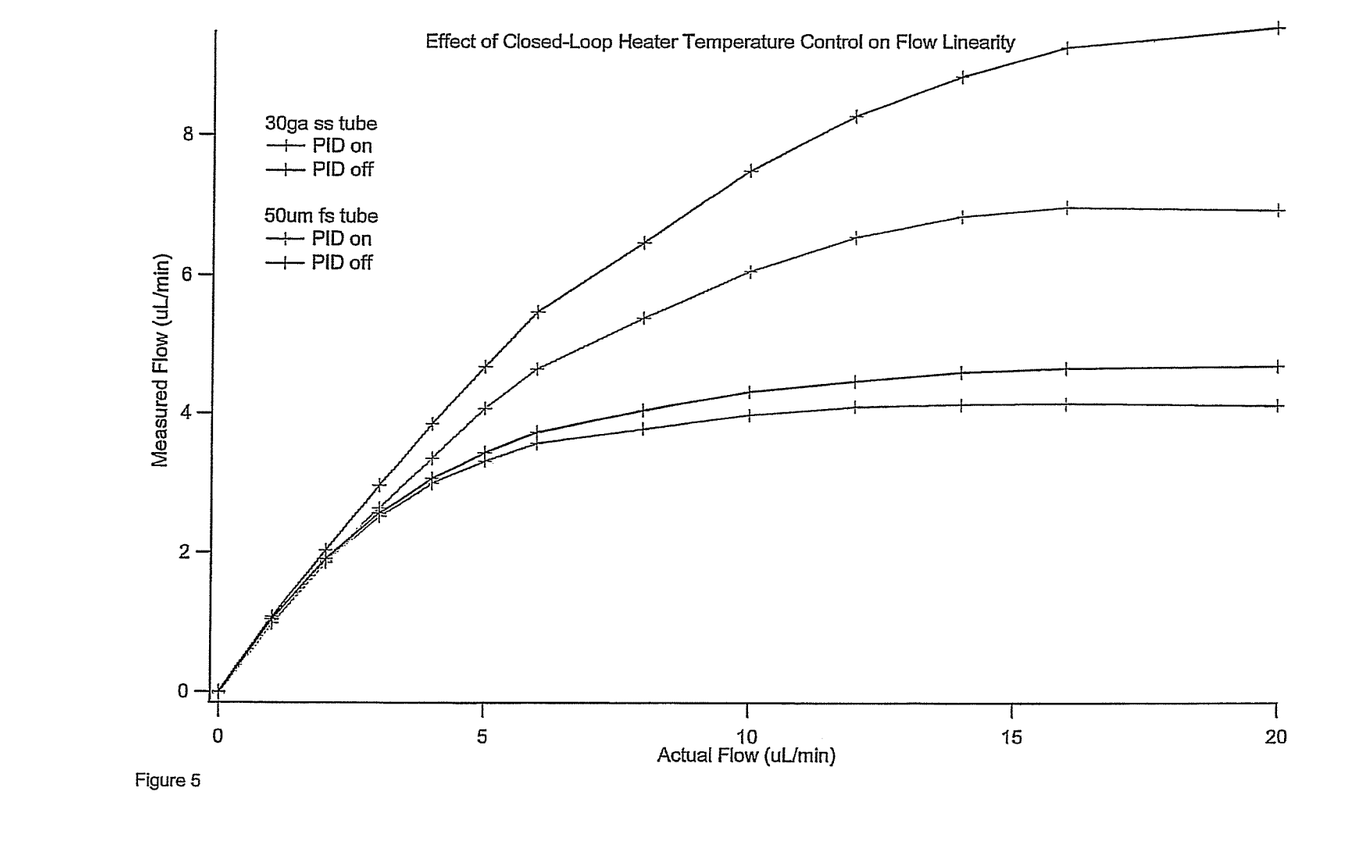
FIG. 5 is a plot of flow rate measurement linearity in relation to actual flow rates.

FIG. 5 depicts the improved linear range of a flow sensor when the temperature of the heater is controlled.

Figure 6:
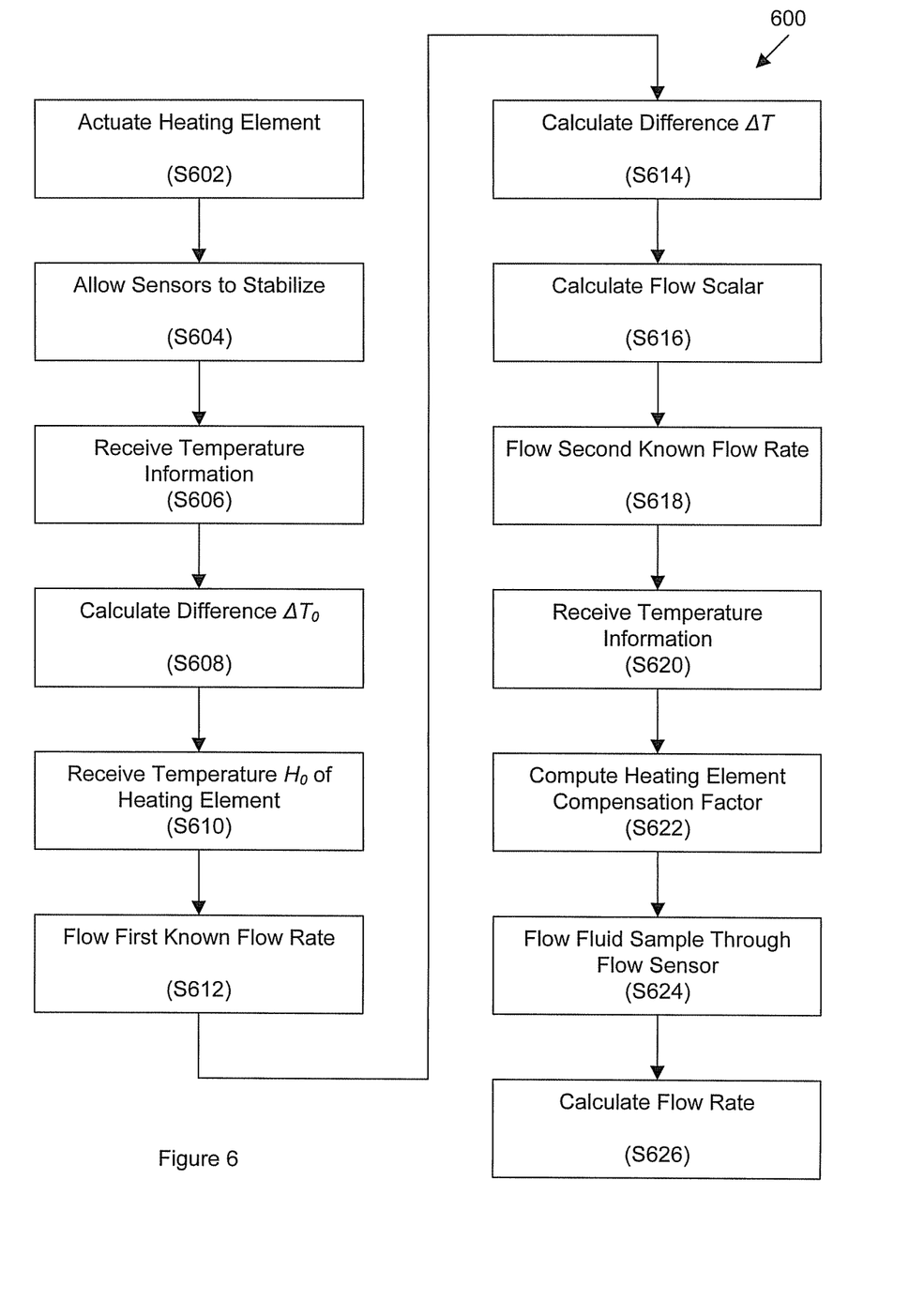
FIG. 6 depicts a method of calculating a flow rate through a flow sensor according to one embodiment of the invention.

Referring now to FIG. 6, a method 600 of calculating a flow rate through a flow sensor is provided. The method 600 can, in some embodiments, be used in conjunction with a flow sensor including a conduit, a first temperature sensor and a second temperature positioned along the conduit, a heating element positioned substantially equidistant between first temperature sensor and the second temperature sensor along the conduit, and a heating element temperature sensor.

In step S602, the heating element is actuated.

In step S604, the temperature sensors are allowed to stabilize/equilibrate until a stable temperature reading is obtained. The time allotted for stabilization can range from several second to several minutes depending on the characteristics of the particular temperature sensors utilized in the flow sensor.

In step S606, temperature information is received from the first temperature sensor and the second temperature sensor.

In step S608, a difference $\Delta T_0$ is calculated between the temperature provided by the second temperature sensor and the first temperature sensor at a zero flow state.

In step S610, a temperature $H_0$ of the heating element is obtained from the heating element at the zero flow state.

In step S612, a first known flow rate is flown through the flow sensor. In some embodiments, the first known flow rate is or approximates the maximum linear range of the flow sensor. For example, the first known flow rate can be between about 0.9 and about 1.0 times the maximum linear range of the flow sensor. The maximum linear range can be determined for a particular flow sensor by observation as discussed herein or can be specified (e.g., by a manufacturer of a flow sensor).

In step S614, a difference ΔT is calculated between the temperature measured by the second temperature sensor and the temperature measured by the first sensor while both temperatures are exposed to a first known flow rate.

In step S616, a flow scalar value based on data received from the first temperature sensor and the second temperature sensor (as reflected in difference ΔT). The flow scalar value can, in some embodiments, be calculated according to Equation (6) above.

In step S618, a second known flow rate is flown through the flow sensor. Preferably, the second known flow rate exceeds the maximum linear range of the flow sensor. For example, the second known flow rate can be between about 1.5 to about 10 times the maximum linear range of the flow sensor, such as: between about 1.5 to about 2.5 times the maximum linear range, between about 2.5 to about 3.5 times the maximum linear range, between about 3.5 to about 4.5 times the maximum linear range, between about 4.5 to about 5.5 times the maximum linear range, between about 6.5 to about 7.5 times the maximum linear range, between about 7.5 to about 8.5 times the maximum linear range, between about 8.5 to about 9.5 times the maximum linear range, and the like.

In step S620, temperature information is received from the first temperature sensor, the second temperature sensor, and the heating element temperature sensor while the flow sensor is exposed to the second known flow rate.

In step S622, a heating element compensation factor is computed. A heating element compensation factor $\alpha$ can be calculated according to Equation (7) above.

In step S624, a fluid sample is flowed through the flow sensor. Because of the use of the heating element compensation factor computed in step S622, the flow rate of the fluid sample can be less than, equal to, or greater than the maximum linear range of the flow sensor.

In step S626, the flow rate of the fluid sample is calculated based on a difference in temperatures between the first temperature sensor and the second temperature sensor, the flow scalar value, and the heating element compensation factor. In some embodiments, the flow rate is calculated according to Equation (8) below:

$$\text{Flowrate} = (\Delta T - \Delta T_0)(1 + (\text{HeaterZeroTemp} - \text{HeaterTemp})\alpha)\text{FlowScalar} \quad (8)$$

Figure 7:
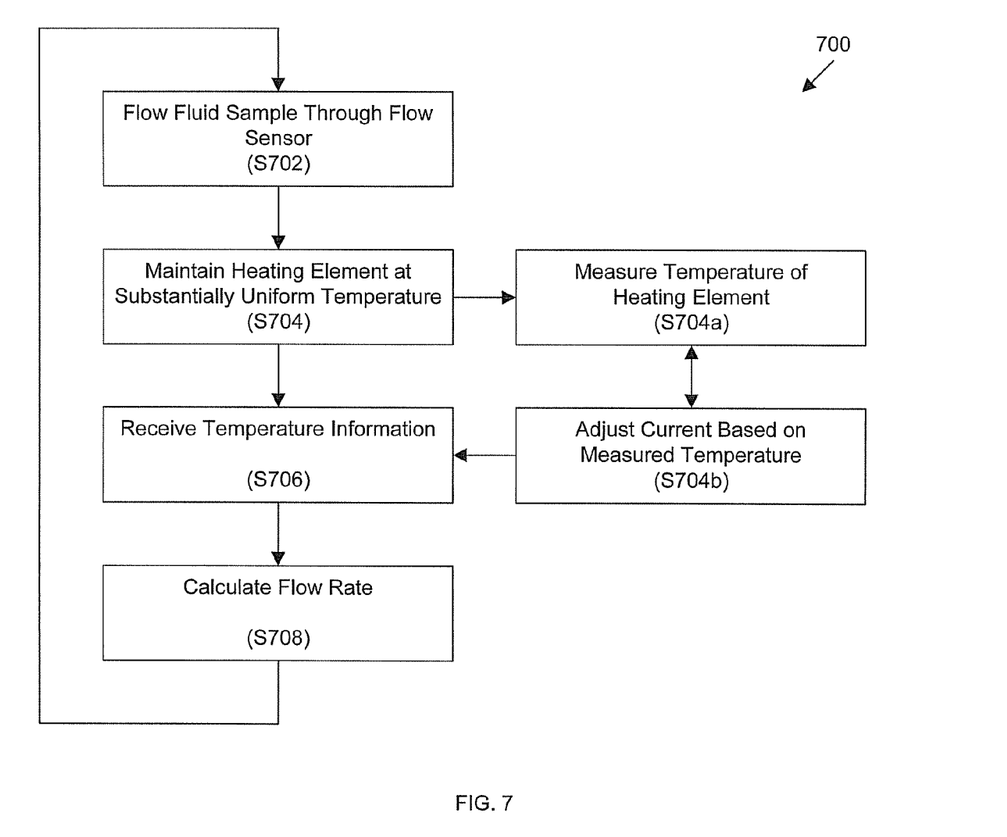
FIG. 7 depicts a method of calculating a flow rate through a flow sensor according to one embodiment of the invention.

Referring now to FIG. 7, another method 700 for determining a flow rate through a flow sensor is provided. Method 700 can, in some embodiments, be used in conjunction with a flow sensor having a conduit, a first temperature sensor and a second temperature sensor positioned along the conduit, and a heating element positioned substantially equidistant between the first temperature sensor and the second temperature sensor along the conduit.

In step S702, a fluid sample is flowed through the flow sensor.

In step S704, the heating element is maintained at a substantially uniform temperature. The heating element can, in some embodiments, be maintained at a substantially uniform temperature by using a temperature sensor to measure a temperature of the heating element (S704a) and adjusting the current flowing across the heater based on the measured temperature of the heating element (S704b).

In step S706, temperature information is received from the first temperature sensor and the second temperature sensor.

In step S708, a flow rate is calculated based on a difference in temperatures between the first temperature sensor and the second temperature sensor.

Implementation in Computer Program Products

The methods described herein can be implemented on general-purpose or specially-programmed hardware or software. For example, methods 600 and/or 700 can be implemented by a computer-readable media. The computer-readable medium can be non-transitory and/or tangible. For example, the computer readable medium can be volatile memory (e.g., random access memory and the like) or non-volatile memory (e.g., read-only memory, hard disks, floppy discs, magnetic tape, optical discs, paper table, punch cards, and the like).

Equivalents

The functions of several elements may, in alternative embodiments, be carried out by fewer elements, or a single element. Similarly, in some embodiments, any functional element may perform fewer, or different, operations than those described with respect to the illustrated embodiment. Also, functional elements (e.g., modules, computers, and the like) shown as distinct for purposes of illustration may be incorporated within other functional elements, separated in different hardware or distributed in a particular implementation.

While certain embodiments according to the invention have been described, the invention is not limited to just the described embodiments. Various changes and/or modifications can be made to any of the described embodiments without departing from the spirit or scope of the invention. Also, various combinations of elements, steps, features, and/or aspects of the described embodiments are possible and contemplated even if such combinations are not expressly identified herein.

INCORPORATION BY REFERENCE

The entire contents of all patents, published patent applications, and other references cited herein are hereby expressly incorporated herein in their entireties by reference.

What is claimed is:

1. A method for determining a flow rate through a flow sensor including a conduit, a first temperature sensor positioned along the conduit, a second temperature sensor positioned along the conduit, a heating element positioned substantially equidistant between the first temperature sensor and the second temperature sensor along the conduit, and a heating element temperature sensor, the method comprising:

actuating the heating element;

receiving temperature information from the first temperature sensor and the second temperature sensor at a zero flow rate;

flowing a first known flow rate through the flow sensor to calculate a flow scalar value;

flowing a second known flow rate through the flow sensor, the second known flow rate exceeding a maximum linear range flow rate of the flow sensor;

receiving temperature information from the first temperature sensor, the second temperature sensor, and the heating element temperature sensor;

computing a heating element compensation factor based on the temperature information received from the first temperature sensor, the second temperature sensor, and the heating element temperature sensor;

flowing a fluid sample through the flow sensor; and calculating a flow rate based on a difference in temperatures between the first temperature sensor and the second temperature sensor, temperature information from the heating element temperature sensor, the flow scalar value, and the heating element compensation factor; thereby determining a flow rate through the flow sensor, wherein the flow rate is defined by $(\Delta T - \Delta T_0)(1 + \alpha(H_0 - H))$ times the flow scalar value, wherein ΔT is a difference between the second temperature sensor and the first temperature sensor while the flow sensor is exposed to the first known flow rate, $\Delta T_0$ is a difference between the second temperature sensor and the first temperature sensor at the zero flow state, $H_0$ is a temperature received from the heating element temperature sensor at the zero flow state by the heating element temperature sensor, H is a temperature received from the heating element at the non-zero flow state by the heating element temperature sensor, and α is a constant.

2. The method of claim 1, further comprising:
calculating the difference $\Delta T_0$ between the second temperature sensor and the first temperature sensor at the zero flow state; and
receiving the temperature $H_0$ of the heating element at the zero flow state from the heating element temperature sensor.

3. The method of claim 1, further comprising:
calculating the difference A T between the second temperature sensor and the first temperature sensor while the flow sensor is exposed to the first known flow rate.

4. The method of claim 1, wherein the first known flow rate is substantially equal to a maximum linear range flow rate of the fluid sensor.

5. The method of claim 4, wherein the flow scalar value is calculated by dividing the known flow rate by the difference between ΔT and $\Delta T_0$.

6. A method for determining a flow rate through a flow sensor including a conduit, a first temperature sensor positioned along the conduit, a second temperature sensor positioned along the conduit, a heating element positioned substantially equidistant between the first temperature sensor and the second temperature sensor along the conduit, and a heating element temperature sensor, the method comprising:
actuating the heating element;
receiving temperature information from the first temperature sensor and the second temperature sensor at a zero flow rate;
flowing a first known flow rate through the flow sensor to calculate a flow scalar value;
flowing a second known flow rate through the flow sensor, the second known flow rate exceeding a maximum linear range flow rate of the flow sensor;
receiving temperature information from the first temperature sensor, the second temperature sensor, and the heating element temperature sensor;
computing a heating element compensation factor based the temperature information received from the first temperature sensor, the second temperature sensor, and the heating element temperature sensor;
flowing a fluid sample through the flow sensor; and
calculating a flow rate based on a difference in temperatures between the first temperature sensor and the second temperature sensor, temperature information from the heating element temperature sensor, the flow scalar value, and the heating element compensation factor; thereby determining a flow rate through the flow sensor; and
receiving a temperature H of the heating element from the heating element temperature sensor while the flow sensor is exposed to the second known flow rate wherein the heating element compensation factor is defined by the expression $(1+\alpha(H_0-H))$, wherein α is a constant according to an expression $$\alpha = \frac{\frac{F}{\Delta T - \Delta T_0} - 1}{H_0 - H},$$

wherein F is the second known flow rate,
wherein ΔT is a difference between the second temperature sensor and the first temperature sensor while the flow sensor is exposed to the first known flow rate, $\Delta T_0$ is a difference between the second temperature sensor and the first temperature sensor at the zero flow state, and $H_0$ is a temperature received from the heating element temperature sensor at the zero flow state by the heating element temperature sensor.

7. The method of claim 6, wherein the second known flow rate F is about three times the maximum linear range flow rate of the fluid sensor.

8. A flow sensing apparatus comprising:
a fluid channel that allows a fluid to flow in a first direction;
a first temperature sensor arranged at a first position along the fluid channel;
a second temperature sensor arranged at a second position along the fluid channel and separated from the first sensor by a predetermined distance along the fluid channel;
a heating element arranged between the first and second temperature sensors, the heating element being substantially equally spaced from the first and second temperature sensors;
a heating element temperature sensor arranged to measure the temperature of the heating element; and
a computing device configured to:
calculate a flow scalar value based on temperature information received from the first temperature sensor and the second temperature sensor while the flow sensor is exposed to a first known flow rate;
calculate a heating element compensation factor based the temperature information received from the first temperature sensor, the second temperature sensor, and the heating element temperature sensor while the flow sensor is exposed to a second known flow rate; and
calculate a flow rate based on outputs from the first temperature sensor, the second temperature sensor, and the heating element temperature sensor, the flow scalar value, and the heating element compensation factor,
wherein the flow rate is defined by $(\Delta T - \Delta T_0)(1+\alpha(H_0-H))$ times the flow scalar value,
wherein ΔT is a difference between the second temperature sensor and the first temperature sensor while the flow sensor is exposed to the first known flow rate, $\Delta T_0$ is a difference between the second temperature sensor and the first temperature sensor at the zero flow state, $H_0$ is a temperature received from the heating element temperature sensor at the zero flow state by the heating element temperature sensor, H is a temperature received from the heating element at the non-zero flow state by the heating element temperature sensor, and α is a constant.

9. The flow sensing apparatus of claim 8, wherein the computing device is further configured to:
calculate the difference $\Delta T_0$ between the second temperature sensor and the first temperature sensor at a zero flow state; and obtain the temperature $H_0$ of the heating element at the zero flow state from the heating element temperature sensor.

10. The flow sensing apparatus of claim 8, wherein the computing device is further configured to calculate the difference $\Delta T$ between the second temperature sensor and the first temperature sensor at a non-zero flow state.

11. The flow sensing apparatus of claim 10, wherein the computing device is further configured to calculate the flow scalar value by dividing the first known flow rate by the difference between $\Delta T$ and $\Delta T_0$.

12. The flow sensing apparatus of claim 11, wherein the first known flow rate is substantially equal to a maximum linear range flow rate of the fluid sensor.

13. A kit comprising a flow sensing apparatus of claim 8 and instructions for installation and/or use.

14. A High Performance Liquid Chromatography (HPLC) device comprising a flow sensing apparatus of claim 8.

15. A flow sensing apparatus comprising:
a fluid channel that allows a fluid to flow in a first direction;
a first temperature sensor arranged at a first position along the fluid channel;
a second temperature sensor arranged at a second position along the fluid channel and separated from the first sensor by a predetermined distance along the fluid channel;
a heating element arranged between the first and second temperature sensors, the heating element being substantially equally spaced from the first and second temperature sensors;
a heating element temperature sensor arranged to measure the temperature of the heating element; and
a computing device configured to:
calculate a flow scalar value based on temperature information received from the first temperature sensor and the second temperature sensor while the flow sensor is exposed to a first known flow rate;
calculate a heating element compensation factor based the temperature information received from the first temperature sensor, the second temperature sensor, and the heating element temperature sensor while the flow sensor is exposed to a second known flow rate; and
calculate a flow rate based on outputs from the first temperature sensor, the second temperature sensor, and the heating element temperature sensor, the flow scalar value, and the heating element compensation factor,
wherein the computing device is further configured to obtain a temperature H of the heating element at the non-zero flow state from the heating element temperature sensor; and
wherein the heating element compensation factor is defined by the expression $(1+\alpha(H_0-H))$, wherein $\alpha$ is a constant according to an expression $$\alpha = \frac{\frac{F}{\Delta T - \Delta T_0} - 1}{H_0 - H},$$

wherein F is the second known flow rate,
wherein $\Delta T$ is a difference between the second temperature sensor and the first temperature sensor while the flow sensor is exposed to the first known flow rate, $\Delta T_0$ is a difference between the second temperature sensor and the first temperature sensor at the zero flow state, $H_0$ is a temperature received from the heating element temperature sensor at the zero flow state by the heating element temperature sensor, H is a temperature received from the heating element at the non-zero flow state by the heating element temperature sensor, and $\alpha$ is a constant.

16. The flow sensing apparatus of claim 15, wherein the second known flow rate F is about three times the maximum linear range flow rate of the fluid sensor.

* * * * *